United States Patent [19]

Whitchurch

[11] Patent Number: 4,601,285

[45] Date of Patent: Jul. 22, 1986

[54] ARM SLING DEVICE

[76] Inventor: Patricia A. Whitchurch, 3908 Hickory Hill Dr., Somerset, Ky. 42501

[21] Appl. No.: 501,364

[22] Filed: Jun. 6, 1983

[51] Int. Cl.⁴ ............................................. A61F 5/40
[52] U.S. Cl. ...................................................... 128/94
[58] Field of Search ........................ 128/94, 87 R, 83

[56] References Cited

U.S. PATENT DOCUMENTS

| 2,560,243 | 7/1951 | Peterson | 128/94 |
| 2,750,940 | 6/1956 | Fear | 128/94 |
| 3,559,640 | 2/1971 | Beckett | 128/94 |
| 4,198,964 | 4/1980 | Honneffer | 128/94 X |

Primary Examiner—John D. Yasko
Attorney, Agent, or Firm—Edward M. Steutermann

[57] ABSTRACT

A sling device for supporting a person's arm including a vest having a back, and at least one front lapel where a first fastener is provided adjacent the shoulder of the lapel and second fasteners are provided on the lapel, a strap device having first cooperative securing arrangement adjacent the first end of the strap and a second securing device adjacent the second end of the strap so that the strap can be secured by the first securing arrangement to the first fastening device and the second end of the strap can be secured to the second fastening device by means of the second securing device to form a sling to receive an arm.

The sling can include a second strap to extend transversely from the first strap where the first strap includes third securing device and where the second strap includes a third fastening device to be received in the third securing device of the first strap and also includes a fourth fastening device to be secured to the second fastening device of the vest.

4 Claims, 6 Drawing Figures

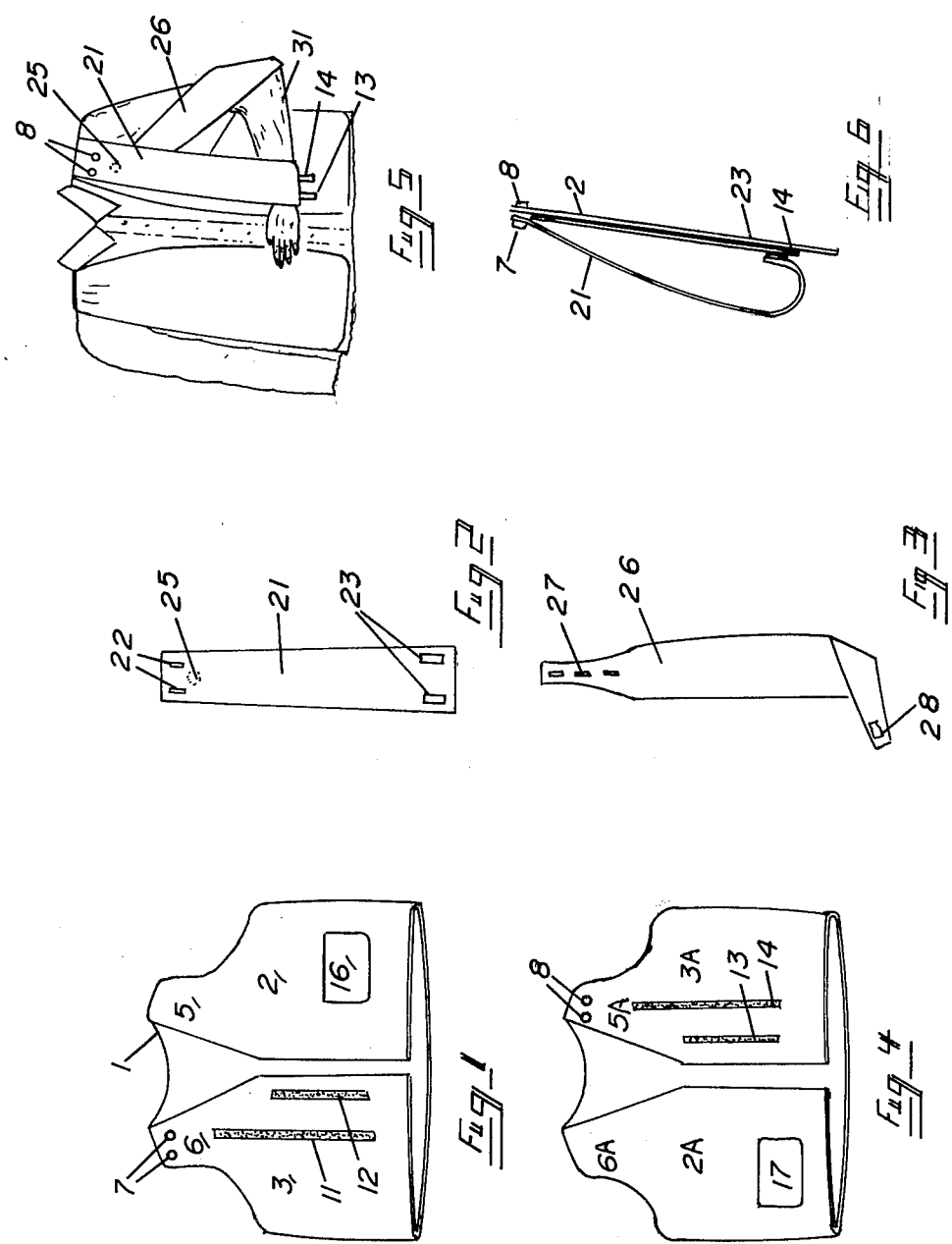

ARM SLING DEVICE

BACKGROUND OF THE INVENTION

The present invention relates in general to sling devices to support an arm of the wearer, for example where the arm has been injured or is in a cast.

In such instances, that is where the arm has been injured and either requires restrictions for movement or where the arm is in a cast so that it is necessary to immobilize the arm to some degree, prior art slings have been utilized where the sling extends around the user's neck and where the arm then rests in the sling. Such prior art arrangements have been uncomfortable in that the brunt of the force exerted by the arm at rest is located on the neck of the user and results in tiring and muscle soreness. Such tiring and soreness occurs particularly where the patient is in a cast so that in addition to the weight of the arm the neck also supports the considerable weight of the cast. Further, prior art slings are unattractive and detract from the appearance of the wearer.

Furthermore, the prior art devices usually provide a knot or other fastener means at the top of the sling so that the adjustment, if any, is localized behind the neck of the wearer and it is extremely difficult, if not impossible, for the wearer to adjust the position of the sling as is required from time to time to change the position of the arm, to overcome fatigue which inherently occurs in the use of such slings.

No prior art device is known to provide an attractive garment which can be utilized as a sling for immobilizing an injured arm or an arm in a cast.

Further no prior art device is known which provides a means for distributing the weight of the immobilized arm, including a cast as the case may be, over the back of both shoulders of the wearer instead of the localizing the supporting force around the neck of the wearer.

SUMMARY OF THE INVENTION

The present invention provides a new and useful arrangement for supporting an immobilized arm where the support device is attractive in appearance and effective in accomplishing the objectives of the immobilization of the injured arm.

Further, devices within the scope of the present invention distribute the force exerted by the immobilized arm over the shoulder of the user rather than concentrating the supporting force around the neck of the user to further reduce the fatigue experienced by the user in using the device.

Additionally, devices within the scope of the present invention provide means for the user to adjust the position of the immobilized arm himself without the need for assistance to adjust the position of the securing device located behind the neck of the user.

Further, the vest within the scope of the present invention can be made reversible so that the same vest can be used for supporting either the left or right arm of the user and can be worn under outerwear.

More particularly, the present invention provides a sling device for supporting a person's arm including a vest having a back, and at least one front lapel where a first fastener is provided adjacent the shoulder of the lapel and second fasteners are provided on the lapel, a strap device having first cooperative securing arrangement adjacent the first end of the strap and a second securing device adjacent the second end of the strap so that the strap can be secured by the first securing arrangement to the first fastening device and the second end of the strap can be secured to the second fastening device by means of the second securing device to form a sling to receive an arm.

The sling can include a second strap to extend transversely from the first strap where the first strap includes third securing device and where the second strap includes a third fastening device to be received in the third securing device of the first strap and also includes a third fastening device to be secured to the second fastening device of the vest.

While the present invention comprehends various arrangements one example of an arrangement within the scope of the present invention is shown in the accompanying drawings but it will be understood that the accompanying drawings and the descriptions relevant thereto are not by way of limitaton but are by way of example only.

BREIF DESCRIPTION OF THE DRAWINGS

The example in accordance with the present invention shown in the Figures:

FIG. 1 is an illustration of a vest within the scope of the present invention;

FIG.2 is an illustration of one strap within the scope of the present invention;

FIG. 3 is an illustration of a second strap within the scope of the present invention;

FIG. 4 is another illustration of the vest of FIG. 1 except shown in the reversed position for use in supporting the left arm of the user;

FIG. 5 is an illustration of the vest of FIG. 4 in position on the user with the first and second straps in position; and FIG. 6 is a elevational view showing the relative orientation of the first strap on the vest.

DETAILED DESCRIPTION OF THE DRAWINGS

Referring now to the illustrations of the Figures, FIG. 1 is an illustration of a vest within the scope of the present invention which includes a back 1, front panels 2 and 3 with lapels 5 and 6 respectively.

The vest shown in FIG. 1 is shown in position for use to support the right arm of the user. The vest however, further includes means to be reversed and to support the left arm of the user as shown in FIG. 4 and described hereinafter. Accordingly buttons 8 are provided on the underside of the lapel 5A where the vest is shown in the reverse position in FIG. 4 with the buttons 8 exposed and the buttons 7 are shown on lapel 5 in FIG. 1.

Within the scope of the present invention second fastener means, for example Velcro (TM) strips 11–12 are provided on front 3A and corresponding strips 13–14 are provided on front 2 as shown in FIG. 4. A pocket 16 can be provided on front 2 and a pocket 17 on front 2A is also shown.

A strap 21 is provided as shown in FIG. 2 and includes buttonholes 22 to receive buttons 7 or 8 as the case may be at the lapel of the vest when the garment is in use and further includes co-operative velcro strips 23 to be received on velcro strips 11 and 12 or 13 and 14 as the case may be depending upon the arm to be supported.

In some instances shoulder subluxation is a problem and in such applications a second strap 26 as shown in FIG. 3 can be provided to provide lateral support to the arm as shown in FIG. 5. Strap 26 includes a series of buttonholes 27 to receive button 25 on the underside of strap 21, as shown in FIG. 2, and also, at the opposite end includes a velcro strap 28 to be selectively attached to one of the velcro straps 11,12,13,14 of the vest.

FIG. 5 is an illustration of the device shown in FIG. 4 in use where an arm 31 is to be supported. As shown strap 21 is connected to lapel 5 by means of buttons 8 which are received in buttonholes 22 and where strap 21 wraps under the wrist of the user and is attached at selected locations to the velcro straps 13–14 by means of the velcro straps 23 (not shown). The second strap 26 is shown extending around the elbow of the user and in this position the buttonhole 27 receives button 25 of the first strap 21.

FIG. 6 is an elevational view of a portion of the arrangement shown in FIG. 5 showing the front panel 2 with the buttons 7 and 8 located on opposite sides of the panel 2 securing the strap 21 in position where the velcro straps 23 are shown received on the velcro straps 13 and 14.

It is recognized that the foregoing is but one example of an arrangement within the scope of the present invention and that various other arrangements also within the scope of the present invention also will occur to those skilled in the art upon reading the disclosure set forth hereinbefore.

The invention claimed is:

1. A sling device for supporting a person's arm including a vest having a back, and at least one front lapel; first fastener means provided adjacent the shoulder on one side of the lapel; second fastener means on the opposite side of the lapel; a strap device having first cooperative securing arrangement adjacent the first end of the strap and a second securing device adjacent the second end of the strap so that said strap can be secured by the first securing arrangement to the first fastening device and the second end of the strap can be secured to the second fastening device by means of the second securing device to form a sling to receive an arm of the person wearing the vest.

2. The invention of claim 1 wherein said sling includes a second strap to extend transversely from the first strap where the first strap includes third securing device and where the second strap includes a third fastening device to be received in the third securing device of the first strap and where said second strap includes a fourth fastening device to be secured to the second fastening device of the vest.

3. The invention of claim 1 wherein one of said first fastener means and said second fastener means includes multiple fastener devices so that the position of said strap device on said first fastener means can be adjusted to raise and lower the position of said sling with respect to said vest.

4. The invention of claim 2 wherein said third fastening device is a button and said third securing device is a buttonhole.

* * * * *